United States Patent [19]

Müller

[11] Patent Number: 5,085,997
[45] Date of Patent: Feb. 4, 1992

[54] METHOD OF SEPARATING YEASTS FROM FERMENTATION LIQUORS

[75] Inventor: Hans Müller, Erlenbach, Switzerland

[73] Assignee: DrM, Dr. Müller AG, Männedorf, Switzerland

[21] Appl. No.: 602,389

[22] Filed: Oct. 22, 1990

Related U.S. Application Data

[63] Continuation of Ser. No. 634,618, Jul. 26, 1984, abandoned.

[30] Foreign Application Priority Data

Jul. 27, 1983 [CH] Switzerland .......................... 4106/83

[51] Int. Cl.⁵ .......................... C12N 1/02; C12N 1/16; C12N 1/18; C12P 7/06
[52] U.S. Cl. .................................... 435/261; 435/161; 435/255; 435/256; 435/311; 435/803; 210/791; 210/798; 210/797; 210/805
[58] Field of Search ............... 435/261, 161, 255, 256, 435/311, 803; 210/791, 797, 798, 805

[56] References Cited

U.S. PATENT DOCUMENTS

| | | | |
|---|---|---|---|
| 1,263,226 | 4/1918 | Genter | 210/798 |
| 1,348,159 | 8/1920 | Down | 210/218 |
| 2,351,970 | 6/1944 | Jansen | 435/261 |
| 4,156,630 | 5/1979 | Muller | 435/261 |
| 4,282,105 | 8/1981 | Crowe | 210/798 |
| 4,306,884 | 12/1981 | Roth | 435/161 X |
| 4,358,383 | 11/1982 | Asp | 210/797 X |
| 4,405,466 | 9/1983 | Giannelli et al. | 210/798 |
| 4,443,421 | 4/1984 | Hollifield et al. | 210/791 X |
| 4,552,669 | 11/1985 | Sekellick | 210/798 |

FOREIGN PATENT DOCUMENTS

| | | | |
|---|---|---|---|
| 0073079 | 3/1983 | European Pat. Off. | 435/311 |
| 587147 | 1/1978 | U.S.S.R. | 435/311 |

OTHER PUBLICATIONS

Peppler, Microbial Technology, New York, Reinhold Publishing, 1967, pp. 442–443.

Primary Examiner—Douglas W. Robinson
Assistant Examiner—Carol Geckle
Attorney, Agent, or Firm—Michael J. Striker

[57] ABSTRACT

In a method of the separation of yeasts from a fermentation liquor contained in a fermentation tank the fermentation liquor is forced by a pump through a conduit system into a filter container in which the fermentation liquor is forced through a number of vertically suspended candle-like filters so that yeast filter cakes are formed on the filter cloth with water of the filters. The cakes are then washed with water, blown off with pressurized air for dewatering, loosened with a counterflow of a pressurized gas and discharged from the filter container. The filter container is immediately connected to the fermentation tank.

11 Claims, 1 Drawing Sheet

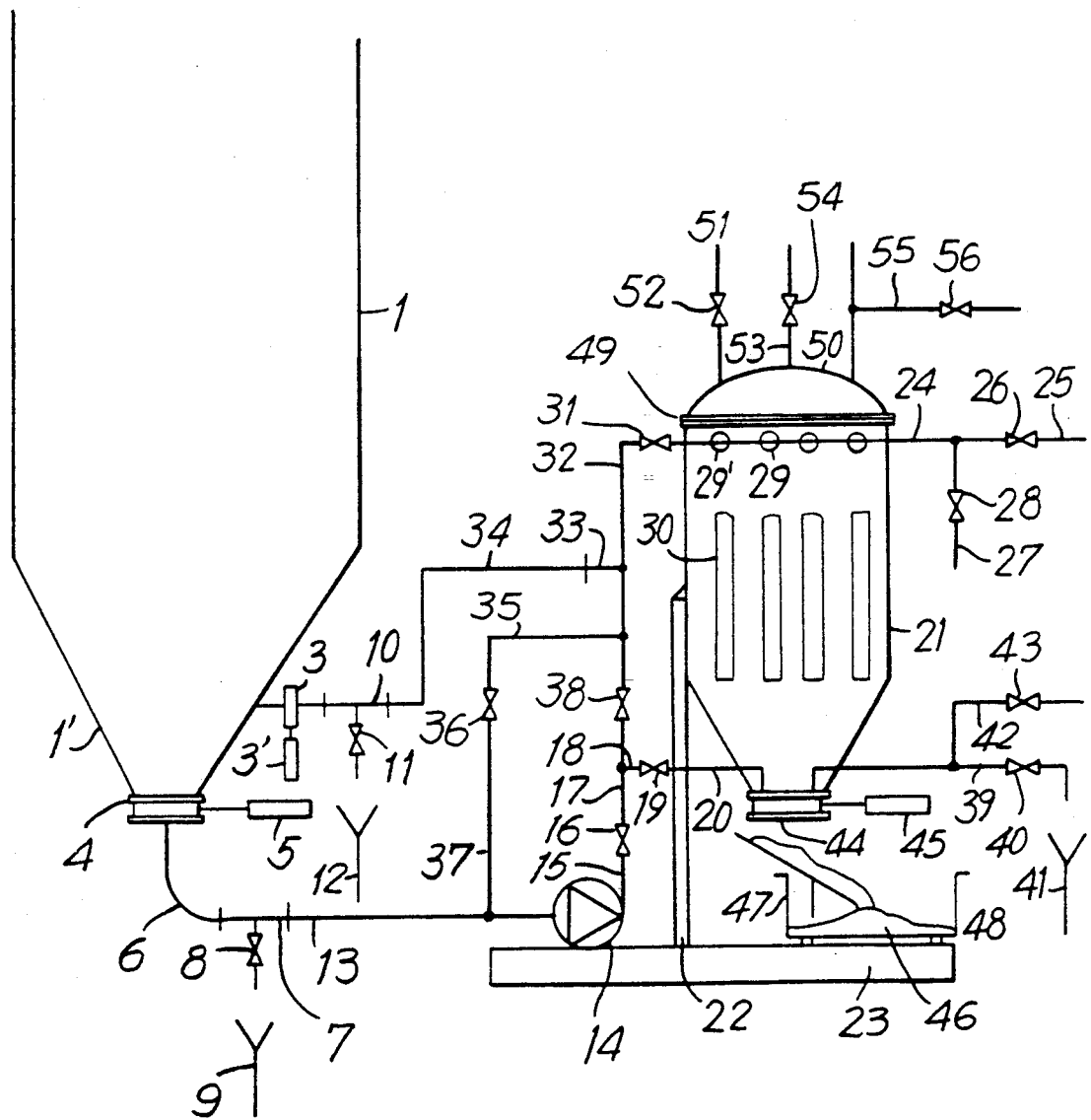

METHOD OF SEPARATING YEASTS FROM FERMENTATION LIQUORS

BACKGROUND OF THE INVENTION

The present invention relates to a method of the separation of yeasts from fermentation liquors produced in fermentation tanks, particularly for producing compressed yeasts to be utilized for baking or compressed yeasts which are deposited from an alcohol fermentation during the production of alcohol beverages, wine or beer.

Methods of separating yeasts from fermentation liquors in chamber filter presses are known. In these methods a yeast suspension is pumped through the filter press unless the chambers of the press are completely filled with yeast. This known process has the disadvantage that the compressed filter cakes built up in the press chambers are very difficult to wash and the removal of these cakes as well as the cleaning of the filter press requires a great deal of hand labor.

It has been also known first to concentrate baking yeasts or yeasts, produced in the alcohol fermentation from fermentation liquors, up to the concentration of the dry substance content of 16-18 weight percent by expensive separators, and then to cool the separated yeasts and dewater them to obtain 29-32 weight percent of the dry substance in a vacuum filter drum with the utilization of a filter medium. This method has the disadvantage that huge amounts of water have been required for washing out the separated yeasts collected in the separators, whereby the washing effect has been relatively insignificant. Another disadvantage of this conventional method resides in high costs of dewatering devices.

SUMMARY OF THE INVENTION

It is an object of the present invention to provide an improved method of separating yeasts from fermentation liquors.

It is another object of the present invention to provide a method of the separation of yeasts from fermentation liquors produced in fermentation tanks under continuously maintained sterile conditions to produce yeasts with the content of the dry substance of at least 29 weight percent.

These and other objects of the invention are attained by a method of separating yeasts from fermentation liquors produced in a fermentation tank for producing compressed baking yeasts and compressed yeasts formed in an alcohol fermentation in an alcohol, wine and beer manufacturing, comprising the steps of providing filter means having a filter container and a plurality of filter elements vertically suspended in the filter container and coated with a filter cloth; discharging a fermentation liquor from the fermentation tank; continuously forcing the fermentation liquor continuously through said filter means in a direction of filtration to filter out said liquor, whereby yeast filter cakes are built up on the filter cloth of the filter elements; washing the filter cakes with a washing liquid; blowing off the filter cakes with a pressurized gas for dewatering; then supplying pressurized gas into the container in a direction opposite to the direction of filtration whereby the filter cakes are loosened from the filter cloth of the filter elements; and discharging the loosened yeast filter cakes from the container.

The pressurized gas or pressurized air is supplied into the container after the blowing-off step to loosen the filter cake in the pressure-pulsating fashion and in the direction opposite to the direction of filtration.

It is particularly advantageous for the filtration stage and the washing-out stage of the process that the filtering surfaces carrying the filter cloth are vertically suspended and therefore are accessible at all sides of the filter. It is also advantageous that the filter cakes built up on those surfaces are also accessible at all sides so that a satisfactory washing of the cakes can be achieved.

The filter container may be immediately connected to the fermentation tank. Therefore it is possible to separate at least a portion of the yeasts from the fermentation liquor contained in the fermentation tank during the fermentation process and under sterile conditions. Thereby any contact of the liquor with air during the separation process is avoided. The yeasts extracted from the fermentation liquor under sterile conditions can be used again. Due to the immediate connection between the filter container and the fermentation tank it is possible to filter out the whole amount of yeasts formed in the fermentation tank in a single filtration stage. Thus the beer losses in the case of the filtration are reduced practically to minimum.

A positive pressure may be constantly maintained in the filter container during the washing step, the blowing-off step and the discharging step, whereby the penetration of foreign particles into the container is prevented.

The washing fluid, e.g. water, may be, dispersed into air in the washing step. Therefore due to atomization fine liquid drops are obtained so that the amounts of washing fluid being used and the time periods of washing are substantially reduced as compared with conventional methods of the foregoing type.

Yeast filter cakes resulted from the filtration step may have the thickness of 10 to 20 mm. With such thickness of the cakes a satisfactory filtration output of 300 to 800 $1/m^3/h$ under filtration pressure of 3-5 bar is available.

The dewatering of the yeast filter cakes, as the filter container is emptied of liquid, frees the yeast cells from a surrounding liquid. It is advantageous that the filter cakes are blown off by air or any other suitable gas for 3-5 minutes, preferably 3 minutes. The consumption of pressure air is thus relatively insignificant. At the beginning of the process, no air penetrates the filter cake. However, after 2-3 minutes of blowing off the cakes begin to crack which defines the end of the blowing-off step.

The short period of the drying time is sufficient to form the filter cakes which contain at least 29 weight percent of an yeast dry substance. As the process of the filtration continues the weight percent of the yeast dry substance reaches 33. Such high content of the dry substance in the yeast filter cakes can be obtained on the filter drums only with the addition of common salt to the filtering process.

The content of the yeast dry substance in the yeast filter cakes may be controlled by a filtration pressure and/or a pressure of the washing liquid.

The filtering-out step and the washing step may be performed in a cycle of 10-40 minutes. For this period of time the entire volumes of the fermentation liquor being treated and of the washing water can be processed in a single tank while in the conventional installations a series of filter devices are required for the same purpose.

It is advantageous that the blowing off the filter cakes is carried out with a preheated air. The period of time of the blowing-off procedure is thus substantially reduced.

The filter container has a filling side and a discharge side; the filter container being directly connected to the fermentation tank at the filling side and at the discharge side, whereby the whole process of the filtration is carried out under sterile conditions.

The method according to the present invention is suitable for a filtration of baking yeasts and for a separation of yeasts during the beer manufacturing and wine manufacturing as well.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The sole figure of the drawing shows a schematic view illustrating a process of the separation of yeasts from fermentation liquors according to the invention.

DETAILED DESCRIPTION OF THE PREFERRED EMBODIMENTS

Referring now to the drawing in detail reference numeral 1 designates a fermentation tank which includes a substantially cylindrical upper portion and a conical lower portion denoted by reference character 1'. A support 2 carrying a valve 3 and a motor 3' connected to valve 3 is fastened to the conical portion 1' of the fermentation tank. A shutting-off valve 4 is mounted in the apex of the conical portion of the fermentation tank, valve 4 being driven or actuated by means of a servomotor 5. The shutting-off valve 4 is connected via a conduit 6 to a tube 7 on which a valve 8, which opens into a line connection 9, is provided. Support 2 is also connected to a tubular portion 10 which in turn carries a valve 11, the latter opening into a line connection or joint 12. A hose connection 13 leads from tube 7 to a pump 14. A pressure conduit 15 leads from pump 14 via a valve 16 to a conduit piece or portion 17, the latter being connected to a branch conduit 18 which via a valve 19 and a feeding conduit 20 leads to a lower conical portion of a pressure filter container 21 of the pressure filter device including a plurality of suspended candle-like filters 30 of the conventional type.

The filter container 21 is secured on a vertical stand or support 22 the lower end of which is fastened to a bottom plate 23. Container 21 of the filter device is further provided with a rinsing or cleansing conduit 24 connected to the feeding conduit 20 and also connected via a valve 26 to a water connection 25 for supplying rinsing water to the container and with a valve 28 for connecting a gas or air connection 27 to the rinsing conduit 24. It is to be understood that any suitable gas and not necessarily air could be supplied to the filter device. Conduit 24 passes through the filter container 21 and has thereon a number of valves 29, 29'. As mentioned above a row of vertical filter candles 30 are suspended on a common tube in the interior of container 21. Only a portion of each filter candle element 30 is shown in the drawing. The number of the filter elements in the filter device normally depends on the size of the filter container. A valve 31 is mounted at the outlet of the conduit 24. A conduit 32 is connected to the other side of valve 31. Conduit 32 has a connection 33 for a hose 34. Conduit 32 also has a branch 35 which leads via a valve 36 to a conduit 37 which is in connection with pump 14. Conduit 32 also leads through a valve 38 to the conduit 17.

A further conduit 39 is provided in the lower portion of the filter container 21, conduit 39 leading through a valve 40 to a condensate discharge 41. A bypass conduit 42 is connected via a valve 43 to a non-illustrated pressure gas source.

A slide 44 provided with a motor 45 serves for extracting rigid residuals or yeasts from a filter container into a conveying device 47 and then into a transporting device 48. The filter container 21 includes a horizontally extended plate 49 on which filter candle-like elements 30 are suspended and to which they are secured. Plate 49 subdivides the interior of filter container 21 into the lower filling space or chamber and the upper space or chamber, which is defined above the filter elements 30 and is a filtering chamber.

A connection conduit 51 for steam and having a valve 52 is in connection with a cover 50 of the filter device. A ventilation conduit 53 with a valve 54, a connection conduit 55 for pressure gas or air and a valve 56, are also mounted to the cover 50.

EXAMPLE I

During the production of beer the filter device is coupled to the fermentation tank 1 and then a sterilization of filter container 21 is carried out. Therefor steam under about 2 bar is supplied via the open valves 40, 29, 29', 19, 16, 38, 31, 11 and 8 into the filter device. This process takes place for 15 minutes. After cooling of the filter device the connection valve 4 is partially opened. Yeast in a suspension state flows through conduit 6, tube 7 and hose 13 into pump 14. The latter pumps the yeast via conduit 15, valve 16, conduit portion 17, branch conduit 18, the open valve 19 and the feeding conduit 20 into the filter container 21. Yeast is deposited on the filter cloth of the candle-like vertical filter elements 30. The filtrate then flows through valves 29, 29', conduit 24, valve 31, conduit 32, hose 24, valve 31, conduit 32, hose 34, tubular portion 10 and open valve 3 back into the fermentation tank 1. After the thickness of the filter cakes, deposited on the filter elements 30, has reached its predetermined value, for example 10-20 mm, the filtration is interrupted and the residual volume is forced back, for example by means of pressurized air supplied from conduit 55, into the fermentation tank 1 through the open valves 19, 38, 36 and 4. Thereafter a blowing off of the yeast filter cakes for dewatering of the latter is performed. To achieve this pressurized air is supplied into the filter container through the open valve 43 and conduit 42 in the direction of filtration while the ventilation valve 54 is open. For the removal of the filter cake which falls toward the bottom of the filter container slide 44 is opened by the electric motor 45 and pressurized air is supplied in a pulsating fashion into the filter container in the direction opposite to the direction of filtration through the valves 29 which are temporatily open one after another. The filter cake in the form of yeast 46 with the content of the dry substance amounted to 29-33 weigh percent, preferably 29-30 weight percent falls onto the conveying device 47, by which the yeast is conveyed into the transporting device or container 48 which is provided with wheels as shown in the drawing and can be moved away from the container 21. Thereafter the filter device is washed by rinsing water supplied into container 21 while valves 26, 54 and 42 are open and the filtering device is emptied through the slide 44.

It is possible with the above described device to filtrate the amounts of yeasts deposited in the fermentation tank 1 in one filtration cycle.

EXAMPLE II

The filtration of baking yeasts produced in the fermentation tank 1 is as follows:

A predetermined amount of the yeast suspension is continually pumped through the adjustable valve 4, conduit 6, tube 7, hose 13, pump 14, conduit 15, valve 16, conduit portions 17 and 18, valve 19 and feeding conduit 20 into the container 21 of the filtering device. The yeast suspension has a concentration of 3-5% of yeast dry substance. After filter container 21 has been filled the yeast is deposited on the cloth of the candle-like suspended filter elements 30. The filtrate, which is practically free of yeast, can be discharged from container 21 via conduit 24 and valve 26. If at the first seconds or minutes of the process the filtrate is not sufficiently clear, it is fed back into fermentation tank 1 through the open valve 31 while valves 26, 28, 36 and 38 are closed.

Upon filtering the yeast suspension for about 10 minutes under the feeding pressure of about 5 bar yeast filter cakes of the thickness of 10 to 20 mm, preferably 10-12 mm are built up on the cloth of the filter elements 30. Now the pump 14 is shut off and pressure air under the pressure of about 2 bar is supplied through the open valve 56 and connection conduit 55 into container 21. The residual yeast suspension accommodated in container 21, under pressure of the air, is either forced back into the fermentation tank 1 through the open valve 19, conduit 18, valve 38, hose 34 and valve 3, or is filtrated in a non-illustrated filter device via conduits 39, 42 and valve 43. After the residual volumes of the yeast have been discharged from container 21 a positive pressure is always maintained in the container so that filter cakes would be pressed against the outer surface of the filter cloth of each filter element. The washing water is now pumped by pump 14 into the filter container 21 for about 5-8 minutes so that the filter cakes are washed out. The brown dirty water leaves filter container 21 via conduits 24 and 25 while valve 26 is open.

After the completion of the washing-out stage the residual water present in the container 21 is forced therefrom through conduit 39 by pressurized air supplied into the container from conduit 55. After the washing water has been removed from the container the pressure air under the pressure of 5 bar is forced through the filter cakes via conduits 42 and 39. After 1-2 minutes, at most 3-5 minutes, of this treatment breaks or cracks can be observed on the yeast filter cakes. The drying stage is practically completed. The air consumption in such process is extremely insignificant because the filter cakes are difficult to penetrate by air before the cracks have appeared in the cakes. The yeast filter cake usually contains from 29 to 33 weight percent of the dry substance independently from the pressure of the gas directed onto the cake.

After the completion of the dewatering process slide 44 is opened and the yeast filter cake is released in the counterstream by means of air. The produced yeast is suitable for packing and for an eventual further drying to be used as a dried baking yeast.

It will be understood that each of the elements describe above, or two or more together, may also find a useful application in other types of methods of separation of yeasts from fermentation liquors differing from the types described above.

While the invention has been illustrated and described as embodied in a method of the separation of yeasts from fermentation liquors, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of producing compressed baking yeasts from a fermentation liquid produced in a fermentation tank, wherein filter means having a filter container and a plurality of filter elements vertically suspended in the filter container and coated with a filter cloth are directly connected to the fermentation tank, the method comprising the steps of discharging a fermentation liquor from the fermentation tank and forcing the fermentation liquor continuously through said filter means in the direction of filtration from outside to inside of said filter elements so as to filter out said liquor, whereby a yeast filter cake is built upon the filter cloth of the filter elements; emptying the residual liquor from the filter container; washing said filter cake with a washing liquid; blowing off said filter cake with a pressurized gas for dewatering said filter cake to achieve 29% to 33% by weight of a dry yeast substance; then supplying pressurized gas into said container in a direction opposite to the direction of filtration so that the filter cake is loosened from the filter cloth of said filter elements; and discharging the loosened and dry yeast filter cake from said container.

2. The method as defined in claim 1, wherein said pressurized gas is pressurized air.

3. The method as defined in claim 1, wherein a positive pressure is maintained in said container during said washing step, said blowing-off step and said discharging step.

4. The method as defined in claim 1, wherein said washing liquid is water.

5. The method as defined in claim 3, wherein the washing liquid in said washing step is atomized before contact with the cake.

6. The method as defined in claim 3, wherein the built up yeast filter cake has a thickness from 10 to 20 mm.

7. The method as defined in claim 3, wherein said blowing-off step is performed for 3-5 minutes.

8. The method as defined in claim 3, wherein said forcing step is carried out under a filtration pressure and said washing step is carried out with pressurized washing liquid and wherein a content of the yeast dry substance in the yeast filter cake is also controlled by the filtration pressure and by a pressure of the washing liquid.

9. The method as defined in claim 3, wherein said forcing step and said washing step are performed within 10-40 minutes.

10. The method as defined in claim 3, wherein said blowing off the filter cake is carried out with a preheated air.

11. The method as defined in claim 3, wherein said filter container has a filling side and a discharge side, said filter container being directly connected to said fermentation tank at said filling side and said discharge side.

* * * * *